United States Patent
Akaike et al.

(10) Patent No.: US 6,373,069 B1
(45) Date of Patent: Apr. 16, 2002

(54) METHOD FOR EVALUATING AN EPITAXIAL WAFER FOR A LIGHT EMITTING DEVICE, RECORDING MEDIUM READABLE BY A COMPUTER AND EPITAXIAL WAFER FOR A LIGHT EMITTING DEVICE

(75) Inventors: Yasuhiko Akaike, Kawasaki; Shoichi Washizuka, Yokohama, both of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/395,182

(22) Filed: Sep. 14, 1999

(30) Foreign Application Priority Data

Sep. 17, 1998 (JP) .......................................... 10-263452

(51) Int. Cl.⁷ .............................................. G01N 21/64
(52) U.S. Cl. .................................. 250/459.1; 250/458.1
(58) Field of Search .......................... 250/459.1, 458.1; 438/7

(56) References Cited

U.S. PATENT DOCUMENTS 4,927,778 A * 5/1990 Abbas ......................... 437/51
5,541,416 A * 7/1996 Washizuka ............... 250/458.1

FOREIGN PATENT DOCUMENTS

| JP | 7-50331 | 2/1995 |
|----|---------|--------|
| JP | 8-64652 | 3/1996 |
| JP | 8-316577 | 11/1996 |

* cited by examiner

Primary Examiner—Constantine Hannaher
Assistant Examiner—Otilia Gabor
(74) Attorney, Agent, or Firm—Oblon, Spivak, McClelland, Maier & Neustadt, P.C.

(57) ABSTRACT

An evaluating method capable of quickly measuring the essential lifetime in an epitaxial wafer for a light emitting device independently from the excited carrier density without breaking the epitaxial wafer is configured to obtain the non-radiative lifetime from the changing rate of intensity of luminescence light generated by irradiating exited light onto the epitaxial wafer at the time when the changes with time becomes below a given value, and to obtain the non-radiative lifetime independent from the excited carrier density. An epitaxial wafer for a light emitting device with a higher emission efficiency than conventional ones has a non-radiative lifetime not shorter than 20 nanoseconds obtained by the evaluating method, and the diffusion amount of zinc into its active layer does not exceed 1E13 atoms per cm².

10 Claims, 6 Drawing Sheets

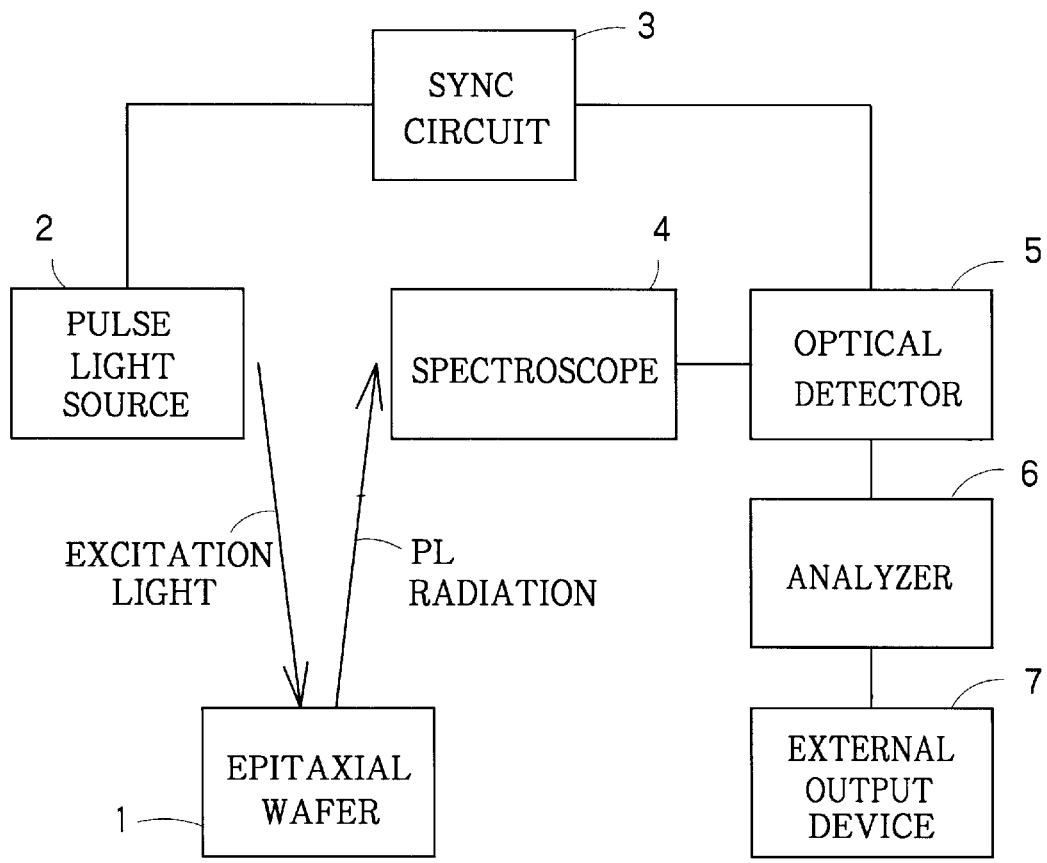
F I G. 1

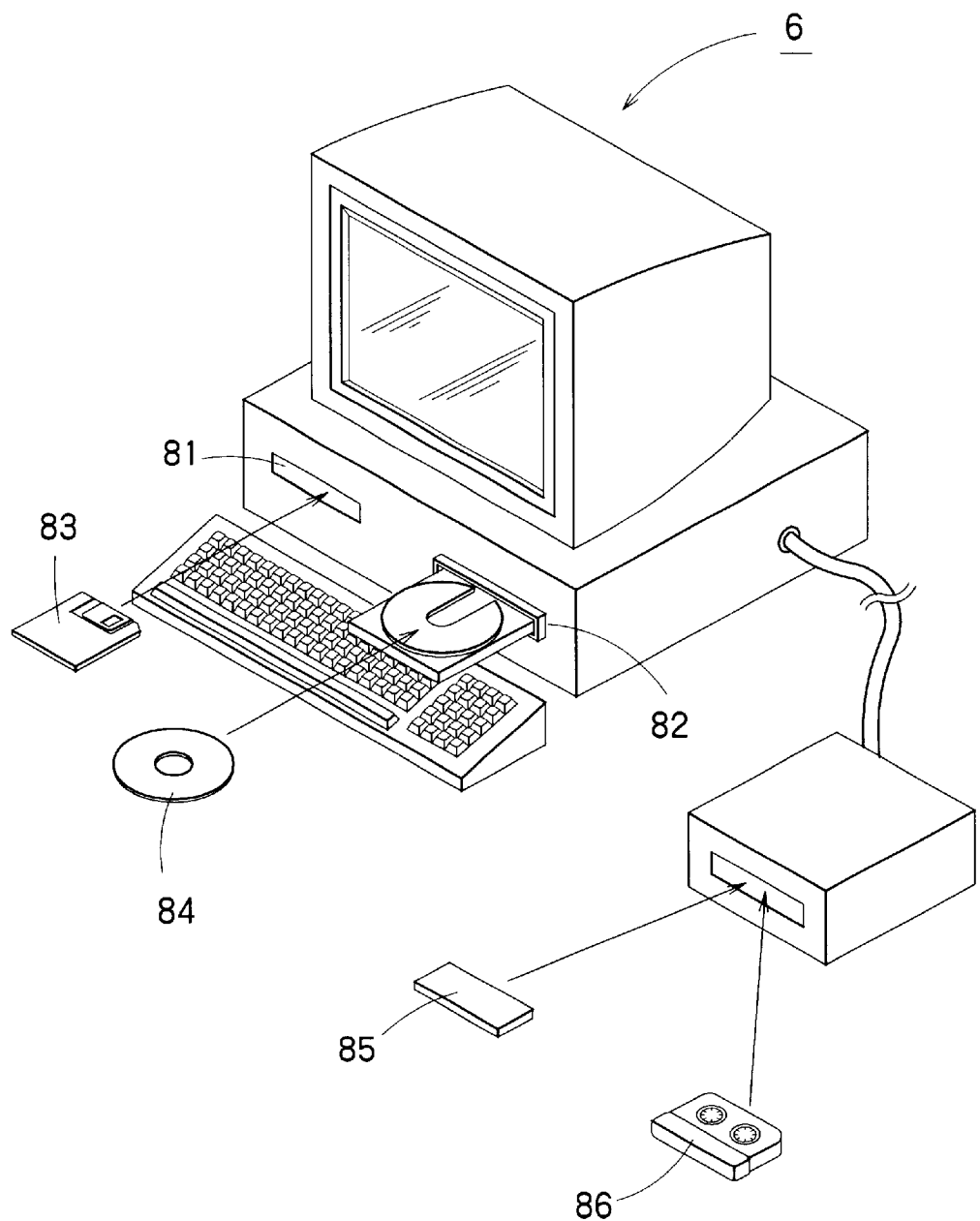
F I G. 2

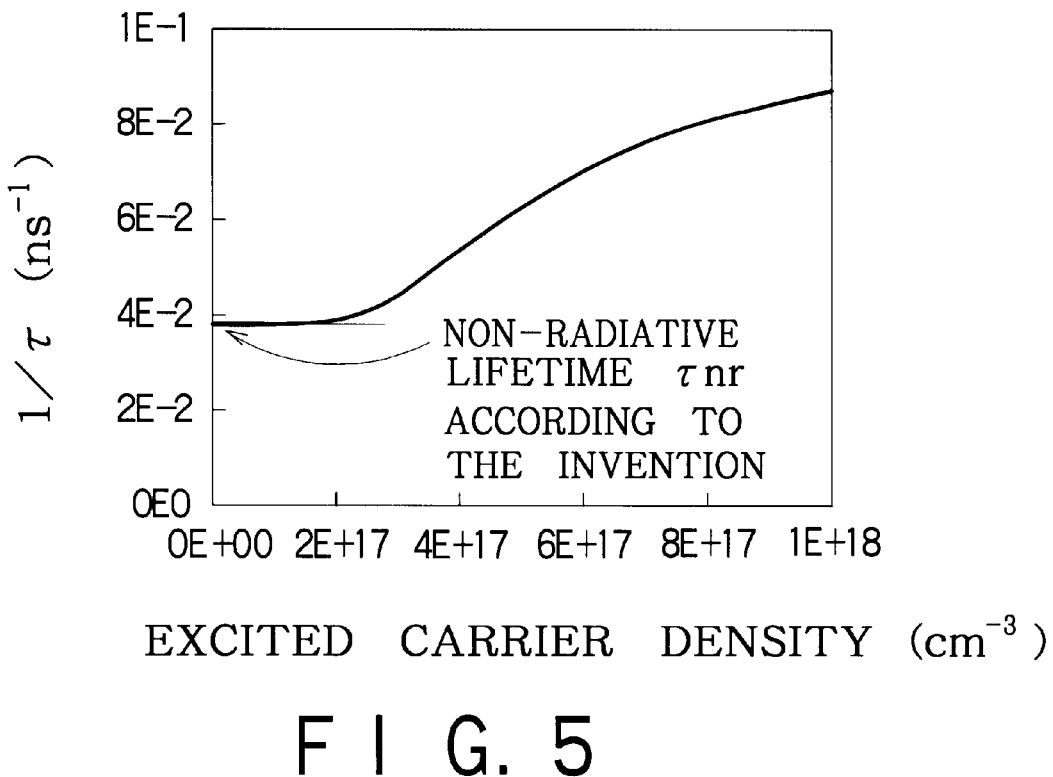
F I G. 5
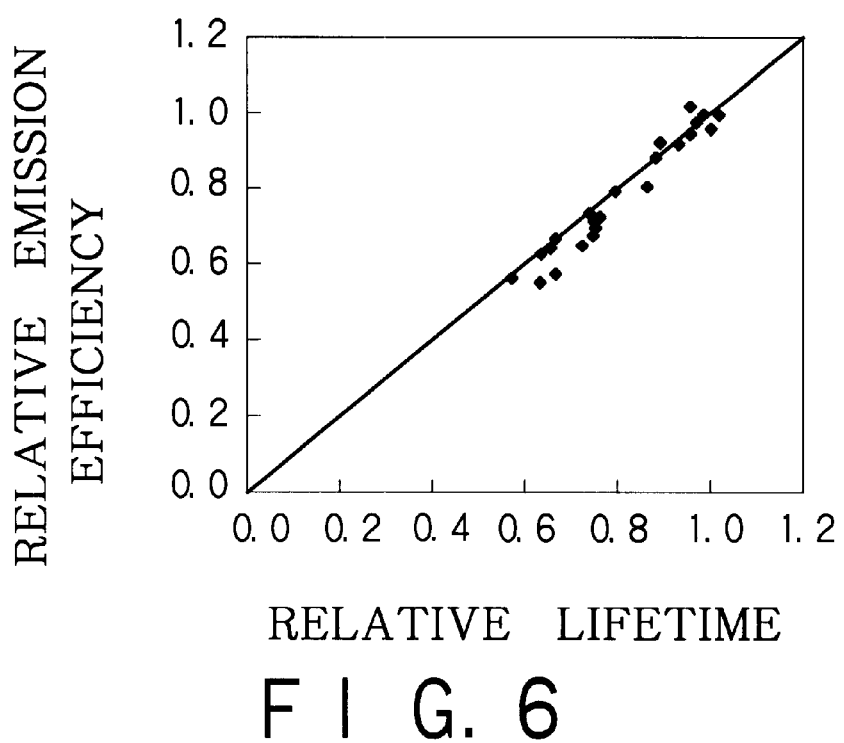
F I G. 6

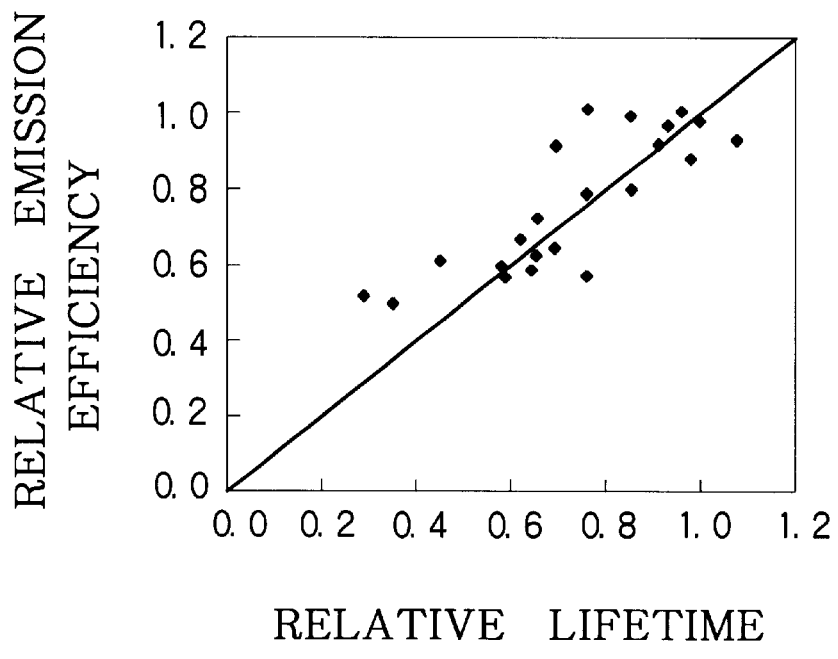
F I G. 7
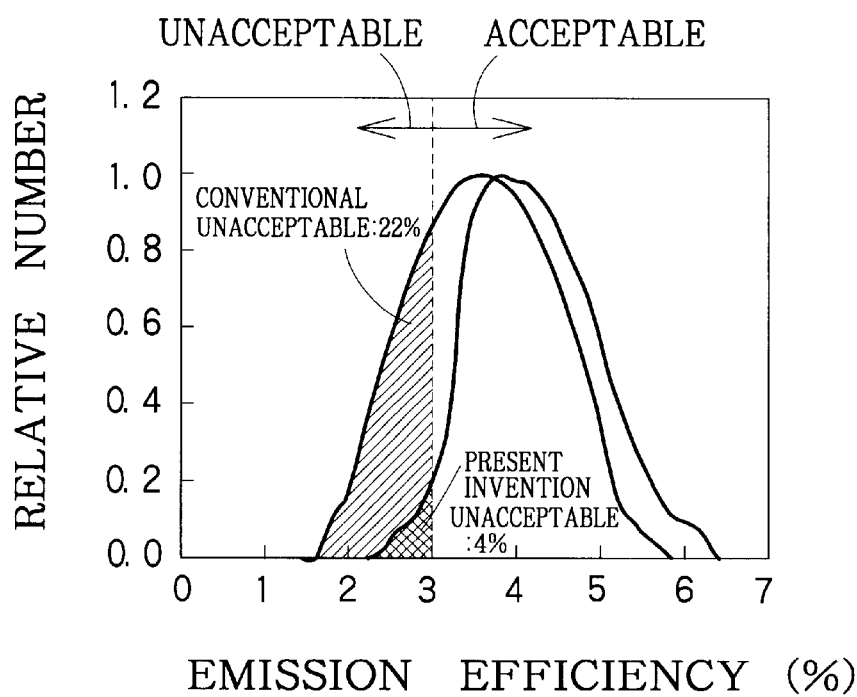
F I G. 8

METHOD FOR EVALUATING AN EPITAXIAL WAFER FOR A LIGHT EMITTING DEVICE, RECORDING MEDIUM READABLE BY A COMPUTER AND EPITAXIAL WAFER FOR A LIGHT EMITTING DEVICE

BACKGROUND OF THE INVENTION

This invention relates to a method and an apparatus for evaluating an epitaxial wafer for a light emitting device, a recording medium readable by a computer, and an epitaxial wafer for a light emitting device. More particularly, the invention relates to an epitaxial wafer useful for providing InGaAlP LEDs excellent in emission characteristics, and an examination method for examining emission characteristics of light emitting devices such as LED and laser diodes, and especially to an examination method capable of precisely evaluating crystallographic properties and emission efficiency of light emitting devices in form of wafers prior to making electrodes thereon.

Along with recent developments of the technology for fabricating films by MOCVD (metal organic chemical vapor deposition), it has become possible to prevent undesirable entry of impurities like oxygen and carbon and crystalline defects along the interface of epitaxial layers (epitaxially grown semiconductor layers), which adversely affect the emission characteristics of LED (light emitting diode), and to manufacture high-luminescence LED by mass-production.

However, it has been difficult heretofore to stably manufacture chips with a high emission efficiency for LED and other light emitting devices because dopants spread in the active layer invited a decrease in luminescence in initial stages of emission and deterioration by electrical conduction.

Regarding InGaAlP LED using Zn (zinc) as its p-type dopant, it has been known that carriers are trapped by a deep level made by Zn diffused into its active layer and large affect its emission characteristics. This phenomenon is explained in, for example, Jpn. J. Appl. Phys. Vol. 33 (1994) pp. L857~L859 "Effect of Substrate Microorientation and Zn Doping Characteristics on the Performance of AlGaInP Visible Light-emitting Diodes", and Solid-State Electron. Vol. 38, No. 2, pp. 305~308. 1995 "AlGaInP Orange Light-emitting-diodes Grown on Misoriented p-GaAs Substrates".

Although Zn has been known as adversely affecting the emission characteristics, relationship between quantities of Zn in the active layer and emission characteristics has not been clarified. In order to fabricate LED epitaxial wafer (wafer with a semiconductor layer epitaxially grown thereon) with good emission characteristics, the diffusion amount of Zn into the active layer should be controlled. However, it is still difficult to precisely control diffusion of Zn in the epitaxial process, and there is no easy measure for evaluating the diffusion amount of Zn. Therefore, it has been difficult to fabricate epitaxial wafers stable in emission characteristics.

That is, heretofore, it was difficult to control diffusion of Zn (zinc) as a dopant, and it was not clear which amount of diffusion of Zn into the active layer deteriorates the emission characteristics.

That is, because of insufficient researches on the relation of the diffusion amount of Zn into the active layer and the emission characteristics, no clear guidance has been given yet regarding the diffusion amount of Zn into the active layer.

To measure the amount of Zn diffused into an active layer, SIMS (secondary ion mass spectroscopy) is typically used. However, this method of evaluation requires a specialized technique. Moreover, it is essentially a destructive inspection, and cannot cope with individuals of wafers which are manufactured in a routine manner.

Conventional techniques involved another problem that emission efficiency could not be measured precisely and easily. That is, although emission efficiency is one of most important factors in optical characteristics of semiconductor light emitting devices, conventional methods were configured to measure the emission efficiency by cutting out a chip from an epitaxial wafer grown in liquid or vapor phase and having formed electrodes. Needless to say, this method requires the process of cutting out the chip. Therefore, it takes much time for cutting out a chip, and quick evaluation of emission efficiency is impossible. Moreover, since a wafer was cut out for evaluation, the production yield inevitably decreased.

As a method for quickly obtaining emission efficiency without touching the subject to be evaluated, there has been proposed an evaluating method using photoluminescence (PL). This is a method for measuring emission efficiency by measuring the lifetime of photoluminescence. For example, Japanese Patent Application No. hei 6-202296 discloses a method for LED having an AlGaAs active layer. Japanese Patent Application No. hei 3-279777 proposes an apparatus combining a probe and an XY stage to measurer such lifetime. Japanese Patent Application No. hei 5-196419 discloses a method for measuring such lifetime in InGaAlP LED and AlGaAs LED by laser excitation.

The reason why emission efficiency can be measured through measurement of lifetime can be explained as follows. Emission efficiency can be expressed by the product of internal quantum efficiency and external quantum efficiency (take-out efficiency). Since the external quantum efficiency may be considered constant among light emitting devices common in structure of the epitaxial layer, electrode pattern and package, emission efficiency depends on the internal quantum efficiency.

Lifetime $\tau n$ can be expressed by the following equation from emitting lifetime $\tau r$ and non-radiative lifetime.

$$1/\tau n = 1/\tau r + 1/\tau n r \quad (1)$$

The internal quantum efficiency can be expressed by the following equation by using the lifetime.

$$\eta i = A \times \tau n / \tau r \ (A \text{ is a constant}) \quad (2)$$

It is noted from Equation (2) that emission efficiency is proportional to the lifetime $\tau n$. Therefore, emission efficiency can be obtained by measuring the lifetime. For obtaining the lifetime $\tau n$, conventional techniques defined the time for photoluminescence radiation to be attenuated from its maximum intensity to 1/e as the lifetime $\tau n$ as explained in the above-introduced three patent applications.

However, since the lifetime $\tau n$ depends upon the emitting lifetime $\tau r$ and the emitting lifetime $\tau r$ is inversely proportional to the excitation carrier density n, the lifetime $\tau n$ also depends on the excitation carrier density n. Therefore, in order to compare different light emitting elements in life time and to discuss their emission efficiency, the premise that they are equal in excitation carrier density n is required.

On the other hand, recent improvements of epitaxial technologies using MOCVD enable accurate control of thickness and composition of thin films, and therefore contributed to realization of LED with a large excitation carrier density, such as visible high-luminescence LED having InGaAlP DH structure (double-heterostructure). As a result, it has become difficult to precisely estimate the emission efficiency by using conventional lifetime measuring methods configured to measure the lifetime without taking the excitation carrier density into consideration because the excitation carrier density was small. This is because excitation carrier density is large in high-luminescence LED, and its effect to the lifetime cannot be disregarded. Therefore, there has arisen the demand for a technique capable of measuring emission efficiency independently from excitation carrier density.

SUMMARY OF THE INVENTION

It is therefore an object of the invention to provide a evaluating method capable of evaluating an epitaxial wafer for a light emitting device, which is capable of quickly measuring the essential lifetime without breaking the wafer, independently from its excitation carrier density. A further object of the invention can be to provide an evaluating apparatus for such evaluation. A still further object of the invention is to provide an epitaxial wafer for a light emitting device, improved in emission efficiency. A still another object of the invention is to provide a recording medium readable by a computer to enable such evaluation.

According to the invention, there is provided an evaluating method for evaluating an epitaxial wafer for a light emitting device, comprising:

irradiating excited light onto the epitaxial wafer;

detecting photoluminescence radiation generated by excitation of carriers in an active layer of the epitaxial wafer; and obtaining the non-radiative lifetime from the rate of changes in intensity of the photoluminescence radiation at the time when changes in intensity of the photoluminescence radiation with time become below a given value.

According to the invention, there is further provided a recording medium readable by a computer, and recording a program for the computer to execute:

a process for having excited light be irradiated onto an epitaxial wafer for a light emitting device;

a process for causing that intensity of photoluminescence radiation generated by excitation of carriers in an active layer of the epitaxial wafer be measured; and a process for obtaining a non-radiative lifetime from the rate of changes in intensity of the photoluminescence radiation at the time when changes in intensity of the photoluminescence radiation with time become below a given value.

The "recording medium" is any of hard disc (HD), DVD-RAM(digital versatile disc-random access memory), DVD-ROM(read only memory), magneto-optical recording medium, flexible disc (FD) and CD(compact disc)-ROM, or any of various memory devices such as RAM and ROM.

A program to be recorded on any of these mediums may be distributed through wire lines orwireless lines such as intranets and Internet in its original form or in a coded, modulated or compressed form, if necessary.

Further, the Inventors made researches on the relationship between the non-radiative lifetime measured by the above-summarized evaluating method and the diffusion amount of Zn into the active layer. As a result, it has been confirmed that, in case of an epitaxial wafer containing the diffusion amount of Zn not less than 1E13 atoms per $cm^2$ in surface concentration, the non-radiative lifetime decreases as the Zn diffusion amount increases. Therefore, in order for an epitaxial wafer to ensure realization of LED with a high emission efficiency, the diffusion amount of Zn into its active layer has to be limited within 1E13 atoms/$cm^2$, and its non-radiative lifetime must be 20 nanoseconds or longer. By using this wafer, LED with high luminescence and stable characteristics can be manufactured.

According to the invention, the true non-radiative lifetime in an active layer can be measured precisely and easily, independently from its excitation carrier density. As a result, epitaxial wafers having a high emission efficiency can be selected reliably, and the production yield is improved remarkably.

That is, according to the invention, in the stage of an epitaxial wafer, defective wafers and acceptable wafers can be discriminated. Therefore, outlet of defective wafers can be prevented, and the production yield is improved. For example, the ratio of defective wafers because of low luminescence is drastically reduced from 22% to 4% as shown in FIG. 8.

Additionally, according to the invention, an epitaxial wafer having a non-radiative lifetime not shorter than 20 nanoseconds can be obtained, and by limiting the diffusion amount of Zn into the active layer within 1E13 atoms per $cm^2$, much better emission characteristics than conventional ones can be realized.

As explained above, the invention makes it easy to discriminate satisfactory wafers from defective wafers, or vice versa, and improved the production yield. Additionally, since the invention enables measurement of emission efficiency indispensable for fabrication of light emitting devices with a high accuracy, profitable industrial effects are expected.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings:

FIG. 1 is a block diagram showing a basic structure of an evaluating apparatus according to the invention;

FIG. 2 is a bird's-eye view generally showing hardware as an analyzer 6 in the evaluating apparatus shown in FIG. 1;

FIG. 5 is a graph plotting excitation carrier density along the abscissa and values of lifetime calculated from an approximation of the PL intensity attenuation curve along the ordinate in the present invention;

FIG. 6 is a graph showing correlation between the lifetime measured by the invention and emission efficiency of LED;

FIG. 7 is a graph showing correlation between the lifetime measured by a conventional method and emission efficiency of LED;

FIG. 8 is a graph showing degrees of emission efficiency in relative value for individual chips of InGaAlP LED wafers evaluated by the invention;

DETAILED DESCRIPTION OF THE PREFERRED EMBODIMENTS

Figure 3:
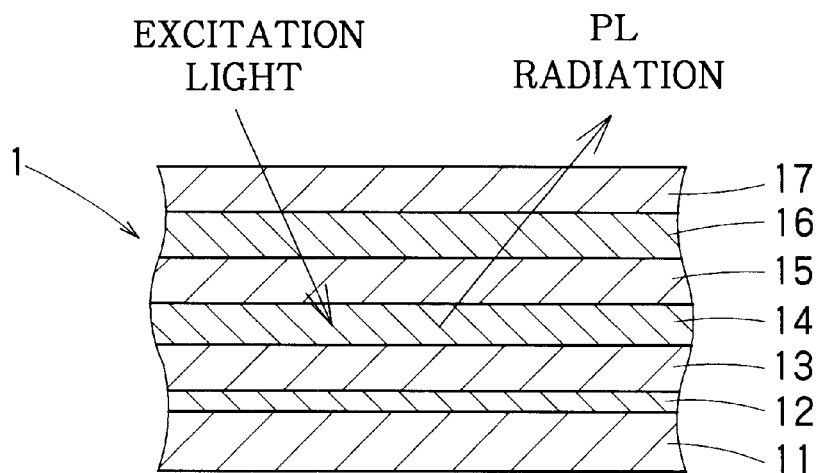
FIG. 3 is a cross-sectional view roughly illustrating the structure of Sample 1.

The Inventors have reached the invention of a method for judging acceptance of epitaxial wafers without breaking it by using measurement of PL lifetime as a result of his own researches. According to this method, non-radiative lifetime can be obtained precisely without breaking the wafers, and acceptance of emission efficiency of the wafers can be known from the result of the measurement. Therefore, outlet of defective wafers to the assembling process can be prevented.

More specifically, laser light is irradiated onto the surface of an epitaxial wafer to have its active layer generate photoluminescence radiation. For this purpose, it is sufficient for the wafer to be so configured that the laser light reaches the emission layer and the photoluminescence radiation excited by the laser light can be taken out externally. Therefore, the wafer may have semi-transparent layers (whose absorptance is lower than 100%) to incident light and photoluminescence radiation, such as electrodes, contact layer and cladding layer, on the active layer.

The photoluminescence radiation is converged into an electric signal, and an attenuation curve of the photoluminescence radiation is approximated in the sum of quadratic or higher-ordered exponential function from changes of the waveform of the converted electric signal with time. Approximation I(t) can be expressed in form of an equation standardized by the following equation.

$$I(t)=\Sigma A_i \times \exp(-t/\tau_i) \quad (3)$$

where $A_i$ is a coefficient of the exponential part defined to satisfy $I(0)=1$, and i is a group of numbers, 1, 2, 3, . . . , and Equation (3) can be decomposed as:

$$I(t)=\Sigma A_i \times \exp(-t/\tau_i)=A_1 \times \exp(-t/\tau_1)+A_2 \times \exp(-t/\tau_2)+ \ldots$$

Although conventional methods define the lifetime $\tau_n$ as being the time for the intensity of the photoluminescence attenuation curve to be attenuated to 1/e, the invention defines it being the reciprocal of the rate of change with time of the photoluminescence attenuation curve obtained by differentiating Equation (3) in time as the following equation.

$$\tau_n(t)=-I(t)/(dI(t)/dt) \quad (4)$$

Changes of the lifetime obtained by Equation (4) with time is defined by the rate of change with time K(t) expressed by the following equation.

$$K(t)=d(1/\tau_n(t))/dt \quad (5)$$

The lifetime $\tau(t)$ at the time when K(t) in Equation (5) is approximately 0 is substantially equal to the non-radiative lifetime $\tau_{nr}$. Therefore, by calculating the lifetime substantially equalizing K(t) to 0 with a computer, for example, the non-radiative lifetime $\tau_{nr}$ of minority carriers, which is the natural physical value of the material independent from the excitation carrier density can be obtained.

The above-explained evaluating method preferably uses a computer to carry out the process.

Since $\tau_{nr}$ is a physical value independent from the excitation carrier density, the non-radiative lifetime $\tau_{nr}$ obtained by the above-explained method establishes a good correlation with emission efficiency also in a high-luminance LED with a large excitation carrier density. Therefore, emission efficiency can be estimated more precisely by using the previously obtained correlation between non-radiative lifetime $\tau_{nr}$ and emission efficiency and measuring the emission efficiency from $\tau_{nr}$ rather than using the previously obtained correlation between non-radiative lifetime $\tau_n$ and emission efficiency and measuring the emission efficiency from the lifetime $\tau_n$.

Additionally, as a result of researched about relations between the non-radiative lifetime measured by the above-explained evaluating method and the diffusion amount of Zn into the active layer, the Inventors have found that the growth temperature of the current spreading layer should be decreased about 30 degrees in centigrade than that of the active layer. By employing the refined growth condition, the Inventors have found that the non-radiative lifetime of an epitaxial wafer containing a diffusion amount of Zn as much as 1E13 atoms per $cm^2$ decreases as the diffusion amount of Zn increases. The epitaxial wafers promising realization of LED with a high emission efficiency are obtained by employing the refined growth condition, and in those wafers, diffusion amount of Zn to the active layer is limited within 1E13 atoms per $cm^2$ and their non-radiative lifetime is not less than 20 nanoseconds. By using these acceptable wafers, high-luminance LED stable in characteristics can be manufactured.

Specific examples of the invention are explained below in detail with reference to the drawings.

FIG. 1 is a block diagram showing a basic structure of an evaluating apparatus according to the invention. In FIG. 1, a sample 1 is an epitaxial wafer of a light emitting device including an emission made by growth. A pulse light source 2 for exciting the emission layer is a laser which oscillates at a wavelength capable of selectively exciting the emission layer. Here is used a laser with a short pulse width, such as YAG laser, semiconductor laser or nitrogen laser, for example.

For guiding the laser light from the pulse light source 2 to the sample 1, a lens may be used to focalize the light, or an optical fiber may be used to guide it. The Inventors got the knowledge on the invention proposed here by measuring lifetime of a number of LED wafers with a time-sequential PL measuring device using a streak camera and a nitrogen laser.

A sync circuit 3 is a device for bringing the detection timing of a detector into synchronism with the photoluminescence radiation, using the excited light as a reference. The photoluminescence radiation is converged by an optical fiber, then divided by a spectroscope 4, and converted into electric signals by an optical detector 5. Electric signals obtained there are sent to an analyzer 6, and attenuation is measured therefrom. The analyzer 6 also calculate the lifetime from the photoluminescence attenuation curve obtained, display it, controls the optical detector, sync circuit, spectroscope, etc., processing various data, and displays the result to an external output device 7 such as CRT, printer, storage means, or the like. The analyzer 6 may be a computer, and needless to say, the function of calculating the lifetime can be realized on software of the computer.

FIG. 2 is a perspective view showing a general aspect of the analyzer 6 in the evaluating device according to the invention shown in FIG. 1, which is made up of hardware. The main body of the analyzer 6 includes an analyzing means for analyzing electric signals from the optical detector 5, control means for controlling the sync circuit 3, spectroscope 4, optical detector 5, and so forth, and a CRT display, for example as an external output device. Additionally, the analyzer 6 includes a floppy disc device (floppy disc drive) 81 and an optical disc device (optical disc drive) 82. By inserting a floppy disc 83 into the floppy disc drive 81 or inserting a CD-ROM 84 into the optical disc drive 82 through its inlet, and executing a predetermined read-out procedure, a program stored on these recording mediums can be installed into the system. Furthermore, by connecting a predetermined drive device, a ROM 85 as a memory device used in a game pack, for example, or a cassette tape 86 as a magnetic tape device can be used.

FIG. 3 is a cross-sectional view showing a general structure of the sample 1. In the example shown here, the sample 1 includes an n-type buffer layer 12, n-type cladding layer 13, active layer 14, p-type cladding layer 15, p-type current spreading layer 16 and p-type contact layer 17 sequentially stacked on a substrate 11. The substrate 11 may be made of n-type GaAs, for example, and the buffer layer 12 may be made of n-type GaAs as well. The cladding layers 13, 15 may be made of $In_{0.5}(Ga_{1-y}Al_y)P$ or $Ga_{1-z}Al_zAs$, and the active layer 14 may be made of InGaAlP or GaAs having a band gap smaller than that of the material of these cladding layer. The p-type current spreading layer 16 may be made of p-type GaAlAs, and the p-type contact layer 17 may be n-type GaAs.

An important feature of the lifetime measurement according to the invention lies in measuring emission efficiency without breaking or contacting the wafer. That is, the invention is advantageous in ensuring accurate measurement only with the PL light intensive enough to enable detection by the optical detector 5 even when having the cladding layer 15, current spreading layer 16, etc. on the active layer 14 because non-radiative lifetime does not depend on the excitation carrier density. This also applies when electrodes, contact layer, current blocking layer, etc. additionally overlie the active layer.

Needless to say, the measuring method according to the invention is also applicable to samples already completed as devices, by converging and irradiating excited light onto a microscope, for example. In this manner, measurement of the non-radiative lifetime of devices still in form of wafers makes it possible to quickly distinguishing satisfactory wafers from defective wafers in terms of emission efficiency before dividing them into chips, feed back its result to the epitaxial growth process, and additionally prevent outlet of defective wafers to the subsequent processes. As a result, the production yield is remarkably improved.

Figure 4:
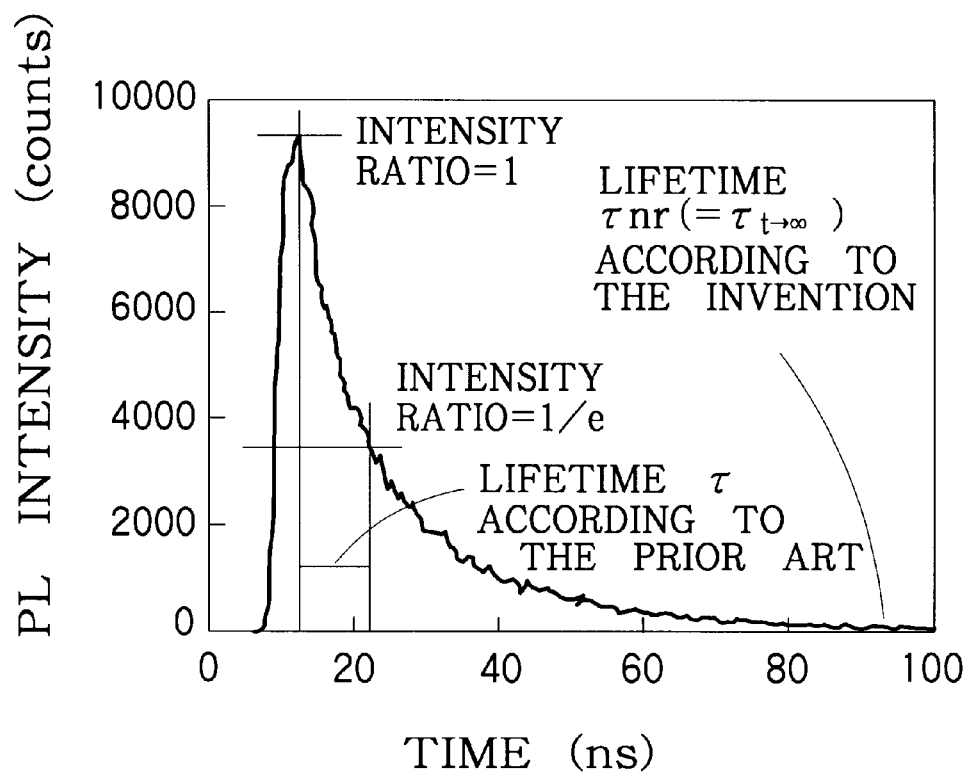
FIG. 4 is a graph showing PL intensity attenuation curve of InGaAlP LED measured by the invention.

FIG. 4 is a graph showing a PL intensity attenuation curve of InGaAlP LED measured by the invention. That is, the graph shows intensity of PL light on the ordinate and time on the abscissa. It is noted from FIG. 4 that carriers are generated by the laser and PL light released upon recombination of these carriers is attenuated with time. The inclination of the PL light attenuation curve is the lifetime, and the lifetime is obtained by differentiating the approximation I(t) of the PL light attenuation curve. Generated carriers decrease with time. Excited carrier density n(t) at arbitrary time t (t>0 here) is defined by the following equation.

$$(n(t)/n(0))=(I(t)/I(0))^{0.5}$$

In this equation, the moment where the laser excites the active layer 14 is assumed as t=0.

FIG. 5 is a graph plotting excited carrier densities by the equation on the abscissa and lifetime values calculated from the approximation of the PL light attenuation curve on the ordinate. The lifetime $\tau n$ is expressed by emitting lifetime $\tau r$, non-radiative lifetime $\tau nr$, recombination constant B and excited carrier density n as follows.

$$1/\tau n=1/\tau r+1/\tau nr=Bn+1/\tau nr$$

In FIG. 5, the curve converges to a constant value in a low carrier density region. This convergent value corresponds to the reciprocal of the non-radiative lifetime independent from the carrier concentration. Therefore, once a excited carrier density dependent graph of lifetime shown in FIG. 4 is obtained from results of the measurement of the PL attenuation curve of any arbitrary epitaxial wafer, non-radiative lifetime can be obtained from the value the graph converges into in a low excited carrier density.

In methods configured to measure emission efficiency from the lifetime of conventional methods, excitation carrier density is not designated upon obtaining the lifetime, and the lifetime is obtained simply from the time taken for the intensity of photoluminescence radiation to decrease to 1/e. Since the excited carrier density is governed by various factors like thickness of the active layer, reflection by the sample surface, incident angle of the excited light, and so on, in addition to the intensity of the excited light, a value of lifetime obtained by a conventional method involves errors by various factors governing the excited carrier density. That is, emission efficiency calculated by such lifetime inevitably results in containing a large error.

The Inventors divided an epitaxial wafer and cut one of the divisional parts into chips for measuring emission efficiency in form of chips while using the other divisional part for measurement in form of the wafer after etching. Lifetime was acquired for both the measurement by the conventional method and the measurement of non-radiative lifetime by the invention, and correlation between acquired lifetime values and emission efficiencies was compared.

FIG. 6 is a graph showing the correlation between the lifetime measured by the invention and emission efficiency of LED.

FIG. 7 is a graph showing the correlation between the lifetime measured by the conventional method and emission efficiency of LED.

It is noted from FIG. 6 that the non-radiative lifetime measured by the invention has a strong correlation with the emission efficiency. In contrast, it is noted from FIG. 7 that the lifetime by the conventional measuring method is much less correlated with the emission efficiency. This difference is considered to evidence that the non-radiative lifetime precisely reflects the crystallographic property of the emission layer so much as it is free from affection of the excited carrier density whereas the conventional method depends on the excited carrier density.

Actually taking a wafer with the emission efficiency of 3.9% calculated from the non-emission lifetime measured by the invention, and providing electrodes on the wafer to complete a device, its emission efficiency was measured electrically. The measured emission efficiency was 4.0%.

FIG. 8 shows, in relative value, degrees of emission efficiency of individual chips from an InGaAlP LED wafer selected by the evaluating method according to the invention. That is, FIG. 8 shows results of measurement of emission efficiency of chips prepared by epitaxially growing an epitaxial wafer by the conventional crystal growth method and dividing it into chips after selection of lifetime by the evaluating method according to the invention. For comparison purposes, FIG. 8 also shows data of emission efficiency of LED wafers evaluated by the conventional evaluating method. Note that the standard of emission efficiency of this kind of LED chips is 3% or more.

In case of wafers selected by the conventional evaluating method, approximately 22% of the total number of chips prepared from defective wafers produced in the process of epitaxial growth were defective. In contrast, when satisfactory wafers alone were delivered to the assembling process by distinguishing acceptance of emission efficiency of chips still in form of epitaxial wafers by the evaluating method according to the invention, defective ones with low emission efficiency were remarkably reduced as low as 4%. That is, the invention enables non-breakage evaluation with much higher accuracy and reliability than conventional one.

Furthermore, the Inventors measured non-radiative lifetime of epitaxial wafers by the evaluating method according to the invention, then fed back its results to growth conditions by MOCVD, and made trial and researches about growth conditions for realizing longer lifetime.

That is, from the result of growing epitaxial wafers for LED by adjusting growth conditions variously and inspecting the lifetime and diffusion amounts of Zn into their active layers, it has been noted that excellent epitaxial wafers can be obtained by adjusting the relation between the growth temperature of the active layer and the growth temperature of the current spreading layer. More specifically, by setting the growth temperature of the current spreading layer 30° C. lower than the growth temperature of the active layer, diffusion of Zn into the active layer can be prevented remarkably, and LED with higher emission efficiency than conventional ones can be obtained reliably.

Figure 9:
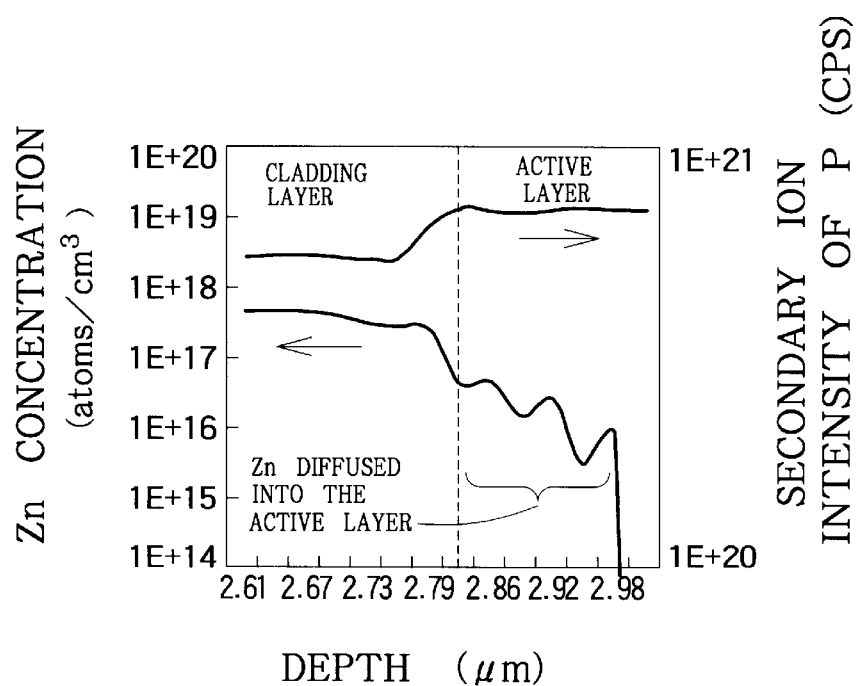
FIG. 9 is a graph showing impurity profiles detected by SIMS in InGaAlP LED made by MOCVD.

FIG. 9 is a graph showing an impurity profile by SIMS of InGaAlP LED wafers prepared by MOCVD. That is, FIG. 9 shows diffusion amount of Zn into the cladding layer and the active layer. In epitaxial wafers prepared by MOCVD, Zn diffused from the p-type cladding layer into the active layer as shown there, and impurity elements Si, C and O were less than the detectable limit. In this fashion, Zn diffused into the active layer behaves as a non-luminescent center which traps carriers, decreases the lifetime of minority carriers, and hence deteriorates the emission efficiency of the light emitting device.

Diffusion amount of Zn into the active layer can be calculated by integrating the Zn concentration in the depth direction from the boundary between the cladding layer and the active layer. Since the cladding layer and the active layer in InGaAlP LED are different in Al composition, a difference in secondary ion intensity of P (phosphor) atoms between the cladding layer and the active layer as shown in FIG. 9. Using this difference, the boundary between the cladding layer and the active layer can be known. The start point of Zn diffusion in the depth direction is determined as the position where the secondary ion intensity of P becomes constant in the active layer side, and the lower limit of Zn concentration is determined as the background level of Zn concentration in SIMS measurement. Steps in SIMS measurement in the depth direction are preferably as many as possible. For conversion of Zn concentration, it is necessary to use standard samples prepared by ion-implanting Zn into epitaxial wafers with the same composition as that of the active layer.

When the diffusion amount of Zn into the active layer was quantified under the above-indicated conditions, the diffusion amount was confirmed to be within 1E13 atoms per $cm^2$ in epitaxial wafers with moderate diffusion of Zn obtained by the invention, and 1E13 atoms per $cm^2$ in epitaxial wafers with severe diffusion amount of Zn obtained by the conventional growth method.

Furthermore, the Inventors measured PL lifetime by the evaluating method according to the invention, taking these epitaxial wafers evaluated in terms of diffusion amount of Zn, and reviewed correlation between the diffusion amount of Zn and the non-radiative lifetime.

Figure 10:
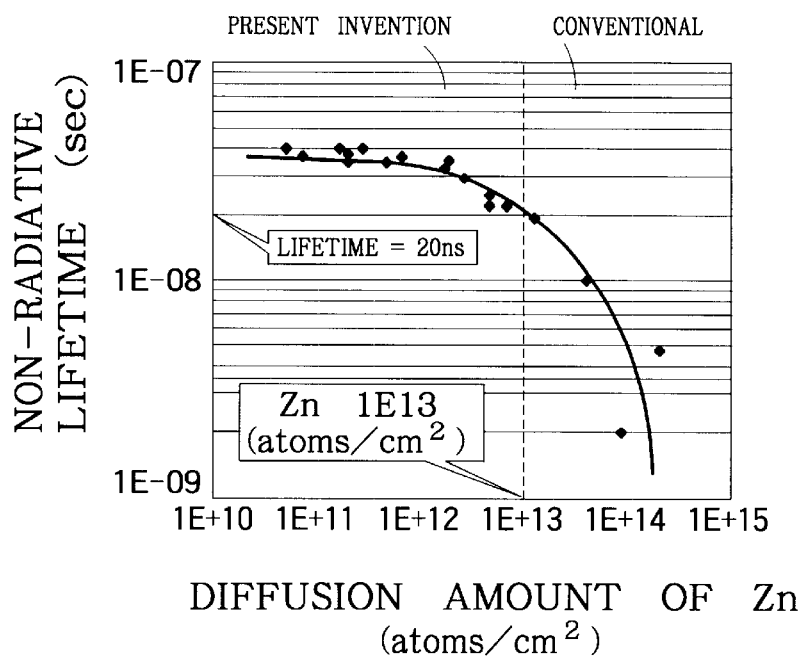
FIG. 10 is a graph showing a relation between diffusion amount of Zn and non-radiative lifetime.

FIG. 10 is a graph showing the relation between the Zn diffusion amount and the non-radiative lifetime. For measurement of the non-radiative lifetime, the above-explained method according to the invention was used. It is noted from FIG. 10 that, in wafers according to the invention, the non-radiative lifetime is 20 nanoseconds or more, and the Zn diffusion amount does not exceed 1E13 atoms per $cm^2$. In contrast, in case of wafers by the conventional method, it is noted that the diffusion amount in the active layer is 1E13 atoms per $cm^2$ or more, and the non-radiative lifetime becomes extremely short as the diffusion amount increases.

As a result of cutting epitaxial wafers by the invention into chips and evaluating them, average emission efficiency was approximately 6%, and much higher emission efficiency than that of conventional epitaxial wafers was obtained. That is, when Zn diffused into the active layer increases to and beyond 1E13 atoms per $cm^2$, Zn dominantly behaves as a non-luminescent center trapping carriers, and reduces the non-radiative lifetime. Reduction of the non-radiative lifetime is equivalent to a decrease of the internal quantum efficiency, and the decrease of the internal quantum efficiency invites a decrease of the emission efficiency.

In contrast, in epitaxial wafers obtained by the invention, the Zn diffusion amount into the active layer did not exceed 1E13 atoms per $cm^2$, the non-radiative lifetime was 20 nanoseconds or longer, and the emission efficiency was confirmed to be remarkably higher than conventional one.

Heretofore, embodiments of the invention has been explained, referring to specific examples. According to the invention, it is possible to significantly improve the production yield of LED.

Then, the method for calculating the non-radiative lifetime and the method for judging the crystallographic quality of epitaxial wafers according to the invention are also applicable to light emitting devices made by using a substrate bonding technology and semiconductor light emitting devices using various materials, such as nitride compound semiconductors (InGaAlN and others), which are materials of blue LED, and other various materials in groups of GaAs, GaP, InP, ZnSe and SiC, for example.

That is, the specific examples can be modified in various modes within the scope of the invention.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

The entire disclosure of Japanese Patent Application No.H10-263452 filed on Sep. 17, 1998 including specification, claims, drawings and summary is incorporated herein by reference in its entirety.

What is claimed is:

1. An evaluating method for evaluating an epitaxial wafer for a light emitting device having an active layer, comprising:

irradiating excited light onto said epitaxial wafer;

detecting photoluminescence radiation generated by excitation of carriers in said active layer of said epitaxial wafer; and obtaining a non-radiative lifetime from a rate of changes in intensity of the photoluminescence radiation at the time when changes in intensity of said photoluminescence radiation with time become below a given value,
wherein said changes in intensity of said photoluminescence radiation with time I(t) is approximated by an equation $$I(t)=\Sigma Ai \times \exp(-t/\tau i)$$

where Ai is a coefficient of the exponential part defined to satisfy I(0)=1, and i is a group of numbers, 1, 2, 3, . . . , with which said I(t) can be decomposed as:

$$I(t)=\Sigma Ai \times \exp(-t/\tau i)=A1 \times \exp(-t/\tau 1)+A2 \times \exp(-t/\tau 2)+ \ldots$$

and said non-radiative lifetime is obtained from a convergent value of a lifetime τn(t) defined by the equation $$\tau n(t)=-I(t)/(dI(t)/dt)$$

with progress of time t.

2. The evaluating method according to claim 1 wherein said lifetime τn(t) is defined by a equation $$K(t)=d(1/\tau n(t))/dt$$

and said non-radiative lifetime is determined to be equal to lifetime τn(t) when K(t) substantially equals to zero.

3. The evaluating method according to claim 2 wherein said epitaxial wafer includes a layer overlying said active layer and having an absorptance to said photoluminescence radiation lower than 100%, and said photoluminescence radiation is detected through said layer.

4. The evaluating method according to claim 2 wherein said epitaxial wafer includes a layer containing zinc as an acceptor.

5. The evaluating method according to claim 4 wherein said epitaxial wafer is determined to be acceptable if said non-radiative lifetime is equal to or greater than 20 nanoseconds.

6. The evaluating method according to claim 4 wherein said active layer includes an InGaAlP layer.

7. The evaluating method according to claim 4 wherein said active layer includes an GaAs layer.

8. A recording medium readable by a computer, and recording a program for said computer to execute:
a process for inputting an intensity of photoluminescence radiation generated by excitation of carriers in a subject to be evaluated; and
a process for obtaining a non-radiative lifetime from a rate of changes in intensity of the photoluminescence radiation at the time when changes in intensity of said photoluminescence radiation with time become below a given value,
wherein said changes in intensity of said photoluminescence radiation with time I(t) is approximated by an equation $$I(t)=\Sigma Ai \times \exp(-t/\tau i)$$

where Ai is a coefficient of the exponential part defined to satisfy I(0)=1, and i is a group of numbers, 1, 2, 3, . . . , with which said I(t) can be decomposed as:

$$I(t)=\Sigma Ai \times \exp(-t/\tau i)=A1 \times \exp(-t/\tau 1)+A2 \times \exp(-t/\tau 2)+ \ldots$$

and said non-radiative lifetime is obtained from a convergent value of a lifetime τn(t) defined by the equation $$\tau n(t)=-I(t)/(dI(t)/dt)$$

with progress of time t.

9. The recording medium according to claim 8 wherein said lifetime τn(t) is defined by a equation $$K(t)=d(1/\tau n(t))/dt$$

and said non-radiative lifetime is determined to be equal to lifetime τn(t) when K(t) substantially equals to zero.

10. The recording medium according to claim 9 wherein said subject is determined to be acceptable if said non-radiative lifetime is equal to or greater than 20 nanoseconds.

* * * * *